US008192494B2

(12) United States Patent
Miz et al.

(10) Patent No.: US 8,192,494 B2
(45) Date of Patent: Jun. 5, 2012

(54) POSTERIOR METAL-ON-METAL DISC REPLACEMENT DEVICE AND METHOD

(75) Inventors: George Miz, Palos Park, IL (US); Richard W. Woods, Catonsville, MD (US); Kevin R. Strauss, Columbia, MD (US)

(73) Assignee: K2M, Inc., Leesburg, VA (US)

( * ) Notice: Subject to any disclaimer, the term of this patent is extended or adjusted under 35 U.S.C. 154(b) by 468 days.

(21) Appl. No.: 11/526,239

(22) Filed: Sep. 25, 2006

(65) Prior Publication Data

US 2007/0083267 A1    Apr. 12, 2007

Related U.S. Application Data

(60) Provisional application No. 60/720,355, filed on Sep. 26, 2005.

(51) Int. Cl.
*A61F 2/44* (2006.01)
(52) U.S. Cl. .................................................. 623/17.14
(58) Field of Classification Search ..... 623/17.11–17.16
See application file for complete search history.

(56) References Cited

U.S. PATENT DOCUMENTS

| 5,676,701 A | 10/1997 | Yuan et al. | |
|---|---|---|---|
| 5,782,832 A * | 7/1998 | Larsen et al. | 623/17.11 |
| 6,395,035 B2 * | 5/2002 | Bresina et al. | 623/17.15 |
| 6,579,321 B1 * | 6/2003 | Gordon et al. | 623/17.16 |
| 6,610,093 B1 | 8/2003 | Pisharodi | |
| 6,706,068 B2 * | 3/2004 | Ferree | 623/17.11 |
| 6,802,863 B2 | 10/2004 | Lawson et al. | |
| 2002/0168508 A1 * | 11/2002 | Reed et al. | 428/308.8 |
| 2003/0208273 A1 * | 11/2003 | Eisermann et al. | 623/17.14 |
| 2004/0138749 A1 * | 7/2004 | Zucherman et al. | 623/17.11 |
| 2004/0260286 A1 | 12/2004 | Ferree | |
| 2005/0085911 A1 | 4/2005 | Link | |
| 2005/0165487 A1 * | 7/2005 | Muhanna et al. | 623/17.15 |
| 2005/0228497 A1 * | 10/2005 | Ferree et al. | 623/17.11 |
| 2006/0085077 A1 * | 4/2006 | Cook et al. | 623/17.15 |

OTHER PUBLICATIONS

Notification of the International Search Report and the Written Opinion of the International Searching Authority, containing the Search Report and Written Opinion, mailed Apr. 26, 2007, containing 8 pages.

* cited by examiner

*Primary Examiner* — Eduardo C Robert
*Assistant Examiner* — Steven Cotroneo
(74) *Attorney, Agent, or Firm* — Carter, DeLuca, Farrell & Schmidt, LLP (57) ABSTRACT

Provided is a device and method for replacing a diseased or damaged intervertebral disc in the spine of a patient. The device provided having at least two units, each of the units having an articulation surface and a bone contacting surface, the articulation surfaces of each of the at least two being in articulating opposition one to the other, one of which having a convex articulation surface and the other having a complementary concave articulation surface. The bone contacting surfaces being provided with bone implantation securing elements such as keel type or spike type protrusions. Also provided is a method of implanting the device into an intervertebral space from a posterior approach.

23 Claims, 10 Drawing Sheets

POSTERIOR METAL-ON-METAL DISC REPLACEMENT DEVICE AND METHOD

BACKGROUND

1. Technical Field

The present invention relates to devices and methods for use in orthopedic spine surgery. In particular, the present invention relates to a device having at least two distinct articulating surfaces, the device being useful as an artificial disc replacement and a method of implanting that device using a posterior approach.

2. Background Art

The human spine is comprised of thirty-three vertebrae at birth and twenty-four as a mature adult. Between each pair of vertebrae is an intervertebral disc, which maintains the space between adjacent vertebrae and acts as a cushion under compressive, bending and rotational loads and motions. A healthy intervertebral disc has a great deal of water in the nucleus pulposus—the center portion of the disc. The water content gives the nucleus a spongy quality and allows it to absorb spinal stress. Excessive pressure or injuries to the disc can cause injury to the annulus—the outer ring that holds the disc together. Generally, the annulus is the first portion of the disc that seems to be injured. These injuries are typically in the form of small tears. These tears heal by scar tissue. The scar tissue is not as strong as normal annulus tissue. Over time, as more scar tissue forms, the annulus becomes weaker. Eventually this can lead to damage of the nucleus pulposus. The nucleus begins to lose its water content due to the damage—it begins to dry up. Because of water loss, the discs lose some of their ability to act as a cushion. This can lead to even more stress on the annulus and still more tears as the cycle repeats itself. As the nucleus loses its water content it collapses, allowing the two vertebrae above and below to move closer to one another. This results in a narrowing of the disc space between the two vertebrae. As this shift occurs, the facet joints located at the back of the spine are forced to shift. This shift changes the way the facet joints work together and can cause problems in the facet joints as well.

When a disc or vertebrae is damaged due to disease or injury standard practice is to remove part or all of the intervertebral disc, insert a natural or artificial disc spacer and construct an artificial structure to hold the effected vertebrae in place to achieve a spinal fusion. In doing so, while the diseased or injured anatomy is addressed and the accompanying pain is significantly reduced, the patients mobility is also reduced, which may have an overall effect on their quality of life.

To that end, there is an overall need to treat the disease or injury while maintaining the six degrees of freedom inherent in the spine. Normal spine anatomy, specifically intervertebral disc anatomy, allows one vertebrae to rotate with respect to its adjacent vertebrae about all three axes. Similarly, the intervertebral disc also allows adjacent vertebrae to translate along all three axes, with respect to one another.

Few devices have been cleared for marketing as an artificial disc replacement by the Food and Drug Administration (FDA). The first device to be cleared by the FDA for use as an artificial disc replacement was the Charité® device by Depuy® Spine. This device has many shortcomings. First, the implantation method for the Charité® device requires an anterior approach to spine surgery. An anterior approach inherently increases the trauma to the patient because an incision must be made in the patient's abdomen and the internal organs must be pushed aside to allow access to the spine. Further, an anterior approach does not easily lend itself to revision surgery due to the amount of scar tissue present from the earlier surgery. This disadvantage is very likely to be encountered because the chance that a revision surgery will be required is higher than a normal fusion because one principal value of a motion preserving device, such as an artificial disc, is that it is indicated for younger patients. Finally, Charité® device and surgical method is such that its initial implantation requires exact alignment due to necessary endplate preparation and if the implantation is performed incorrectly, a subsequent spinal fusion may be required.

Several other similar motion preserving devices have been recently cleared for marketing or are in various stages of clinical trials. These devices include the ProDisc® I and II devices by Synthes, Inc.®, the Maverick® and Prestige® devices by Medtronic Sofamor Danek®, the Flexicore® device by Spinecore, Inc.® and the Bryan Cervical Disc System® by Spinal Dynamics Corporation®. Similar to the Charité® device discussed above, each of these motion preserving devices requires an anterior approach to implant the device in a patient and thus, each of these devices share at least some of the common disadvantages to that procedure. Additionally, some of the devices discussed above utilize a metal-plastic or a plastic-plastic articulating surface wherein the plastic used is thin and typically a form of polyethylene. While articulating surfaces involving plastic have been very successful in other joint replacements, they are subject to varying degrees of implant life and particulate debris, which potentially can cause further damage to the body. Damage caused by particulate debris may become even more critical with spine implants due to the proximity of the spinal cord. Further, many, if not all, of the devices discussed above do not allow for the normal six-degrees of freedom inherent in a natural intervertebral disc.

For the above stated reasons, a need exists for an implantable articulating device, that can be introduced into the body using a posterior approach, similar to a PLIF, T-PLIF or X-PLIF spinal fusion device, can provide the normal six-degrees of freedom for the vertebrae adjacent to the implant, can provide a pro-longed life span in the body that can withstand early implantation, as is often indicated for younger patients, and will have a limited amount of particulate debris so as to reduce complications over the useful life of the device.

SUMMARY OF THE DISCLOSURE

The present invention meets the above identified need by providing a novel articulating device for surgical implantation into a subject. The device and method as disclosed and as claimed herein can be used as an artificial disc replacement that preferably is formed of at least two metallic units, each having an articulating surface having a complimentary conformation to the articulating surface of the other and capable of being surgically implanted from a posterior approach. The opposing articulating surfaces for the at least two units are respectively a convex surface and a concave surface. The device can be implanted in a subject as a unilateral construct or transverse construct. Two pair of articulating surfaced devices can be implanted in a subject to form a bilateral construct if needed. Each pair of articulating surface devices is capable of rotation about all three axes and depending upon the radii of the articulating surfaces, may translate about at least one axis. The device can include additional features to include, for example, compression relief slots to incorporate translational motion about the long axis of the spine. The bone contacting surface of each unit can be configured to include surface textures, materials, or retaining features, such as, for example at least one keel, at least one spike, or other bone position retaining measures. A method of implanting the device, which permits a posterior approach, is also provided.

It is an object of the invention to provide an articulating device having at least two distinct articulating surfaces configured to articulate one to the other.

It is further an object of the invention to provide an articulating device having at least two distinct articulating surfaces configured to articulate one to the other, wherein each articulating surface follows a radius of curvature about at least one axis.

It is further an object of the invention to provide an articulating device having at least two distinct articulating surfaces configured to articulate one to the other, the articulating surfaces being at least one convex surface and at least one concave surface, wherein each of the articulating surface follows a radius of curvature about at least one axis and the radii of curvature for the at least one convex surface and at least one concave surface can be different one from the other.

It is a further object of the invention to provide an articulating device having at least two distinct articulating surfaces configured to articulate one to the other, wherein the articulating surfaces allow rotation of one surface relative to the other about at least one axis.

It is a further object of the invention to provide an articulating device having at least two distinct articulating surfaces configured to articulate one to the other, wherein the articulating surfaces allow translation of one surface relative to the other along at least one axis.

It is a further object of the invention to provide an articulating device having at least two distinct articulating surfaces configured to articulate one to the other, wherein at least one of the articulating surfaces is manufactured of a metallic material.

It is a further object of the invention to provide an articulating device having at least two distinct articulating surfaces configured to articulate one to the other, wherein at least one of the articulating surfaces is manufactured to include a ceramic material.

It is a further object of the invention to provide an articulating device having at least two distinct articulating surfaces configured to articulate one to the other, wherein said articulating surfaces are optimized to reduce friction when articulating movement occurs there between.

It is a further object of the invention to provide an articulating device having at least two distinct articulating surfaces configured to articulate one to the other, wherein said device includes at least three individual units.

It is a further object of the invention to provide an articulating device having multiple articulating surfaces, wherein said device includes at least four individual units, the four units being paired in groups of two units, each paired group including a unit having at least one convex surface and a unit having at least one convex surface, the concave and convex surfaces being configured to articulate one with the other.

It is a further object of the invention to provide an articulating device having multiple articulating surfaces and multiple bone contacting surfaces, wherein said device includes at least four individual units, each individual unit having at least one articulating surface and one bone contacting surface and individual units contacting the same bone surface are capable of being linked one to the other.

It is a further object of the invention to provide an articulating device having at least two distinct articulating surfaces configured to articulate one to the other, wherein the device includes bone contacting surfaces that are configured to improve fixation of the bone contacting surface of the device to the bone of the subject.

It is further an object of the invention to provide a method of implanting an articulating device in the spine of a subject using a posterior approach.

It is further an object of the invention to provide a kit including an articulating device having at least two distinct articulating surfaces configured to articulate one to the other.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DETAILED DESCRIPTION OF PREFERRED EMBODIMENTS

Detailed embodiments of the present invention are disclosed herein; however, it is understood that the following description and each of the accompanying figures are provided as being exemplary of the invention, which may be embodied in various forms without departing from the scope of the claimed invention. Thus, the specific structural and functional details provided in the following description are non-limiting, but serve merely as a basis for the invention as defined by the claims provided herewith. The device described below can be modified as needed to conform to further development and improvement of materials without departing from the inventor's concept of the invention as claimed.

The device, as generally shown at 10 in FIGS. 1, 9A-C, and 10A-D is a disc replacement device that can be configured to provide the six degrees of freedom similar to that of a natural healthy intervertebral disc, the replacement disc being capable of implantation in a subject using a posterior introduction surgical method. The device 10 includes at least two distinct units, a convex articulating surface unit 12 and a concave articulating surface unit 14, which are preferably both manufactured of metallic materials and are configured to articulate one to the other. Each of these units 12, 14 of the device 10 can be provided with elements or structures that can facilitate the successful function and retention of the device.

Figure 1:
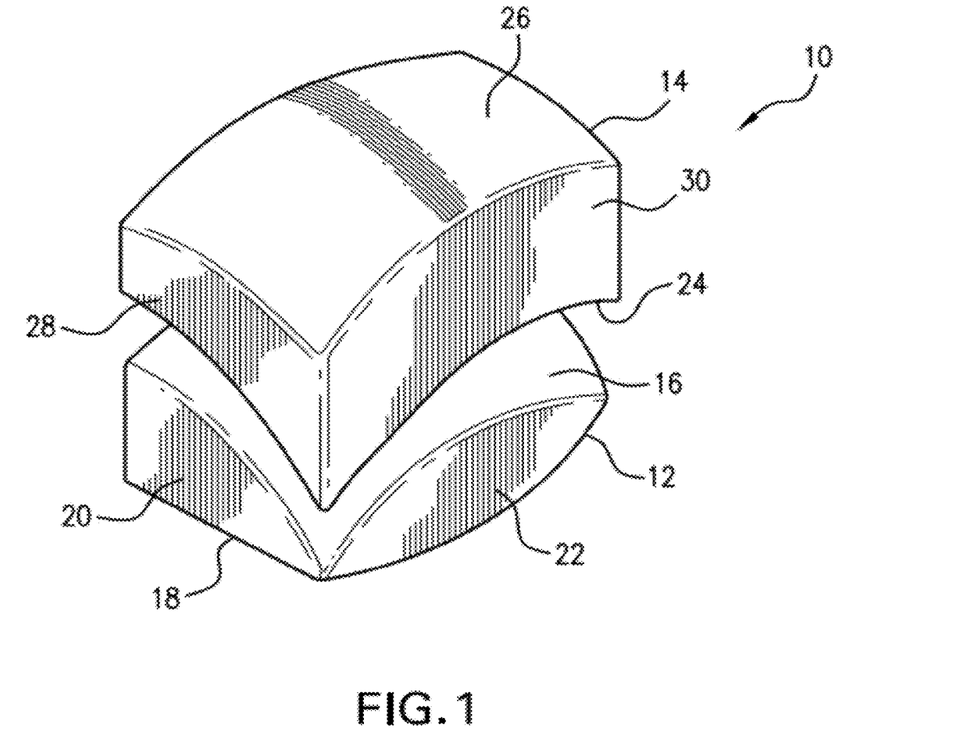
FIG. 1 shows an isometric view of the device including a superiorly disposed unit having a concave articulating surface and a inferiorly disposed unit having a convex articulating surface.
Figure 2A:
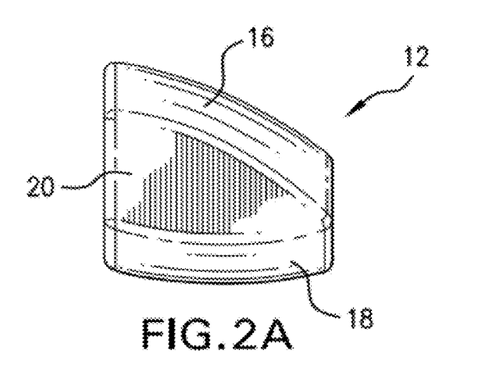
FIGS. 2A-C respectively show a front, side, and isometric view of the unit of the device that has a convex articulating surface.
Figure 2B:
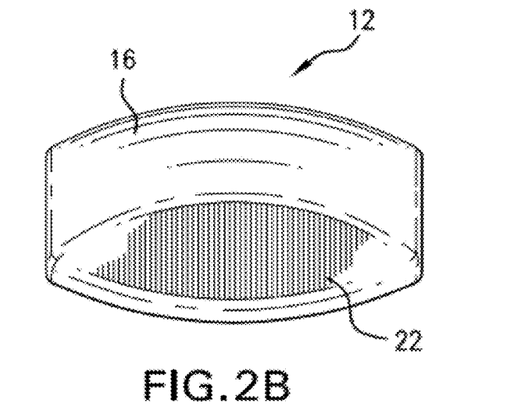
Figure 2C:
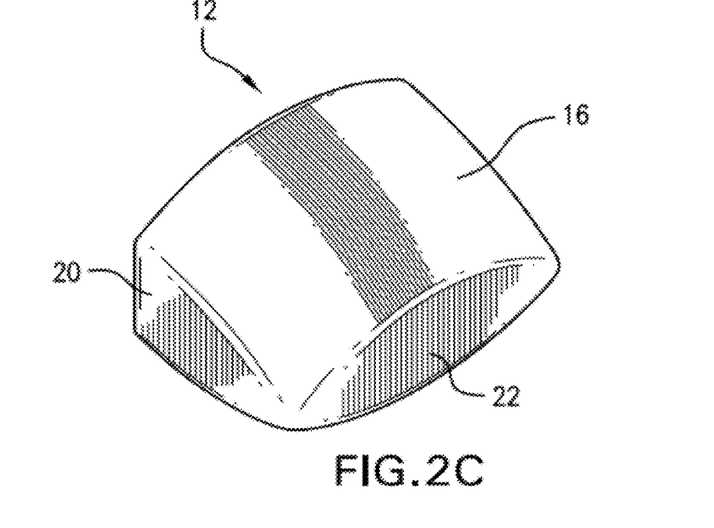

A first embodiment of the convex articulating surface unit (hereinafter, the "convex unit") 12 is shown from various aspects in FIGS. 2A-C. The convex unit 12 includes a convex articulating surface 16, which can be curved about two axes and an opposite convex unit bone contacting surface 18, which can also be curved about two axes. In addition to the articulating surface 16 and the bone contacting surface 18, the structure of the convex unit 12 can also have additional surfaces, which face anterior-posterior 20 and medial-lateral 22 respectively, which contact and interface between the articulating surface 16 and the bone contacting surface 18.

Figure 3A:
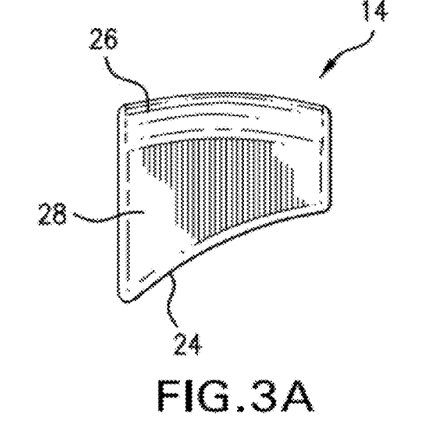
FIGS. 3A-C respectively show a front, side, and isometric view of the unit of the device that has a concave articulating surface.
Figure 3B:
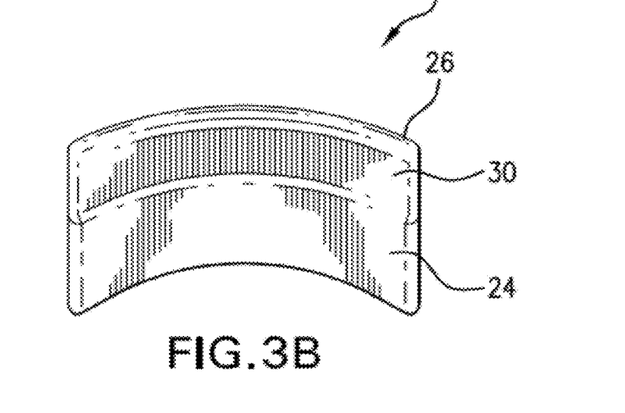
Figure 3C:
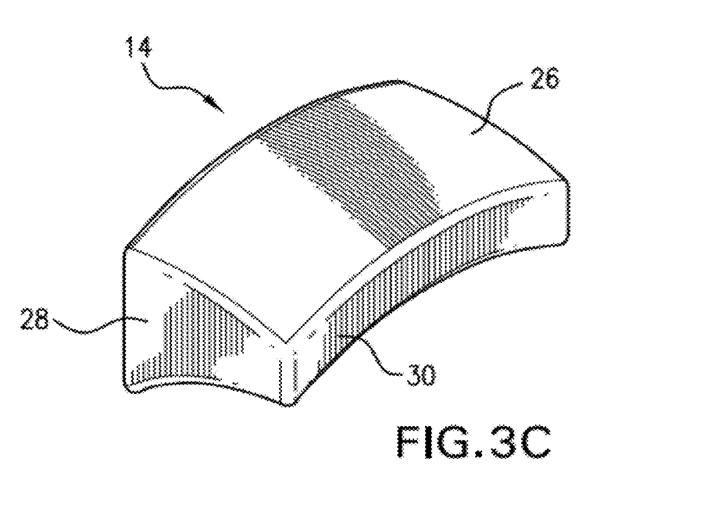
Figure 4A:
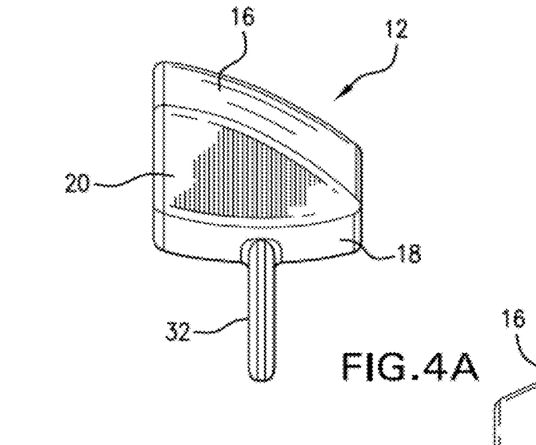
FIGS. 4A-C respectively show a front, side, and isometric view of the unit of the device that has a convex articulating surface and a bone contact surface keel structure projecting from the bone contacting surface of the unit at an approximate right angle.
Figure 4B:
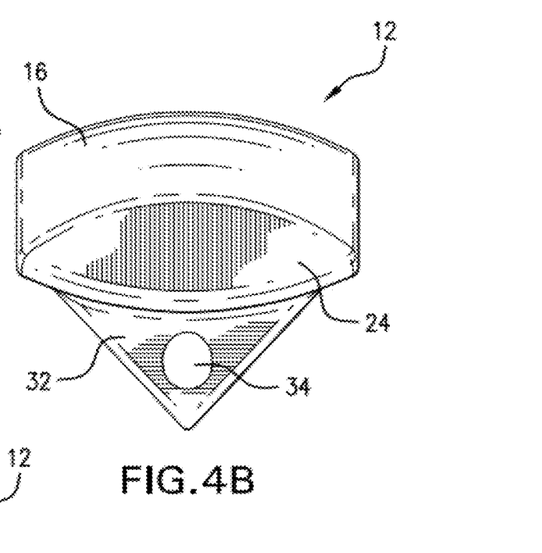
Figure 4C:
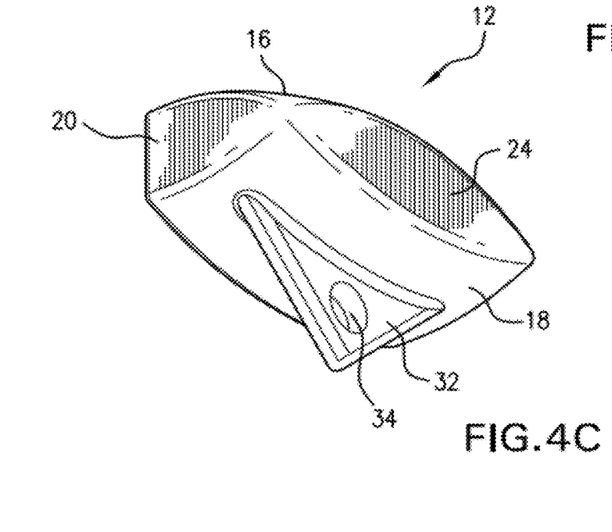
Figures 5A, 5B, 5C:
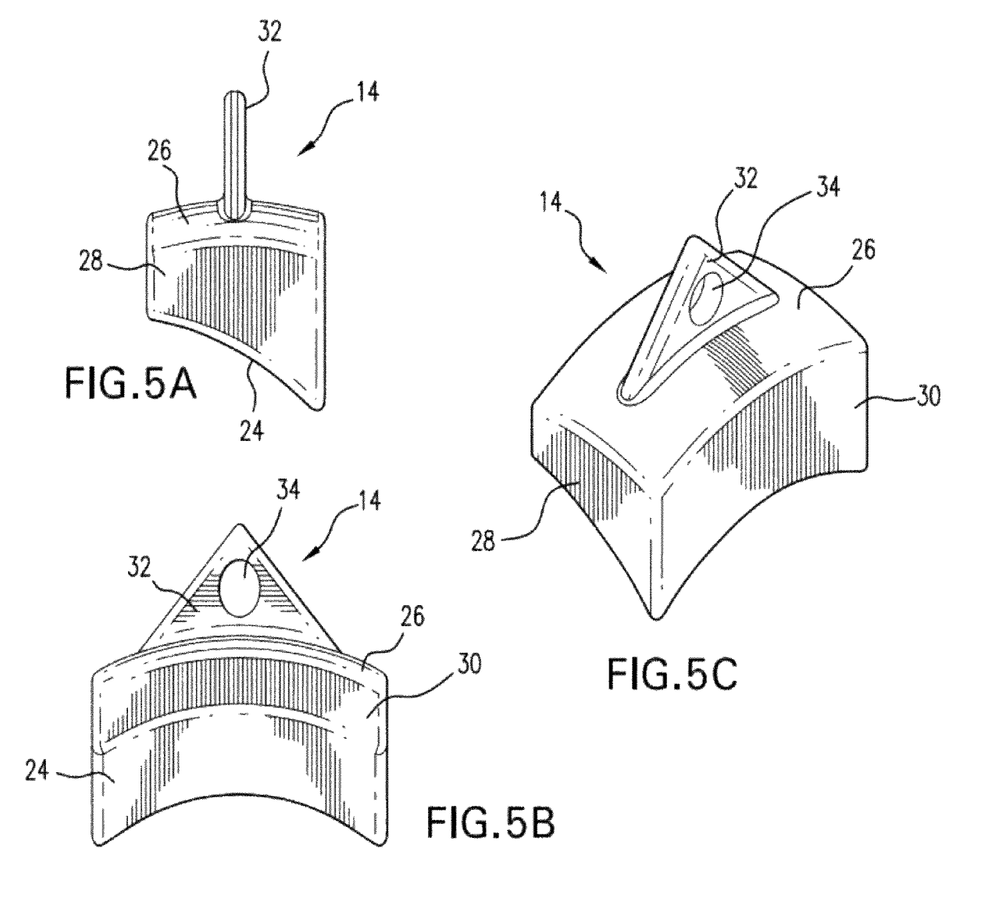
FIGS. 5A-C respectively show a front, side, and isometric view of the unit of the device that has a concave articulating surface with a bone contact surface keel structure.
Figure 6A:
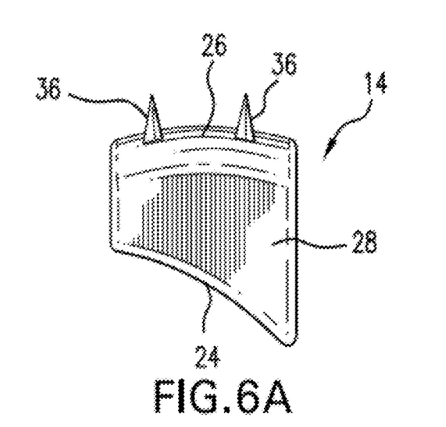
FIGS. 6A-C respectively show respectively show a front, side, and isometric view of the unit of the device that has a concave articulating surface and a bone contact surface having at least one spike.
Figure 6B:
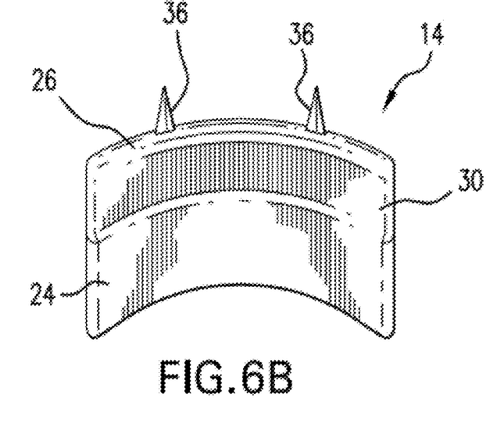
Figure 6C:
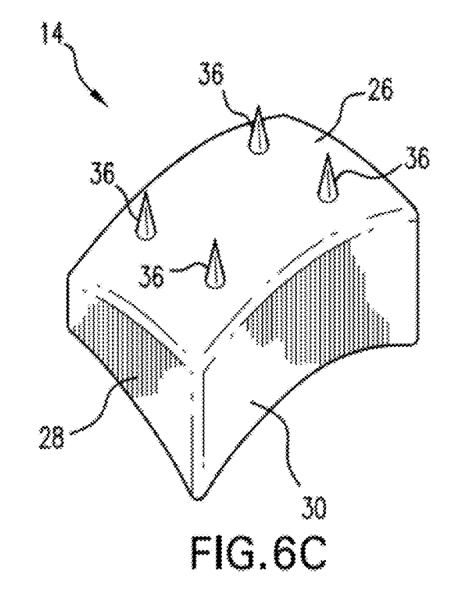
Figure 7A:
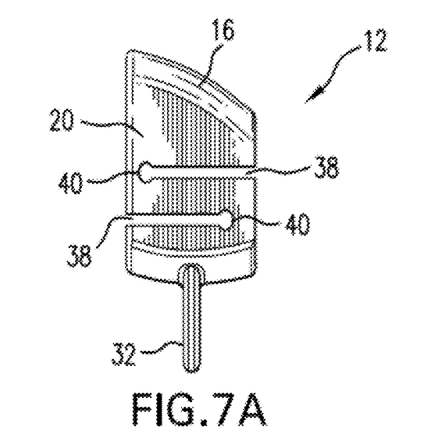
FIGS. 7A-C respectively show a front, side, and isometric view of the unit of the device that has a convex articulating surface, a bone contact surface having a keel structure, and at least one compression relief slot for absorbing compressive forces along the longitudinal axis of the spine.
Figure 7B:
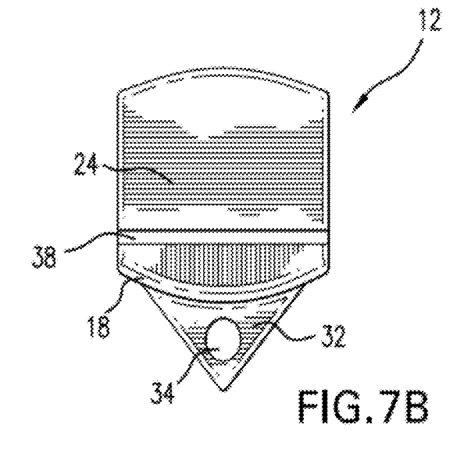
Figure 7C:
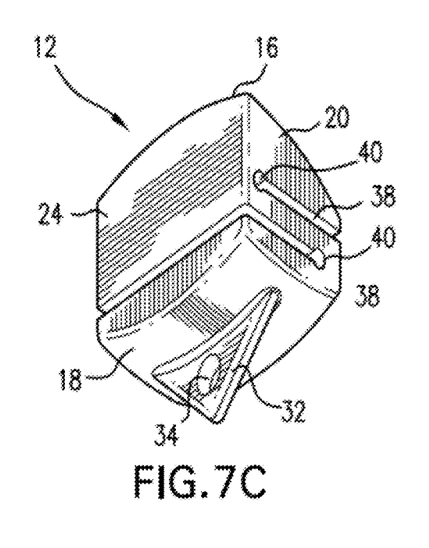
Figure 8A:
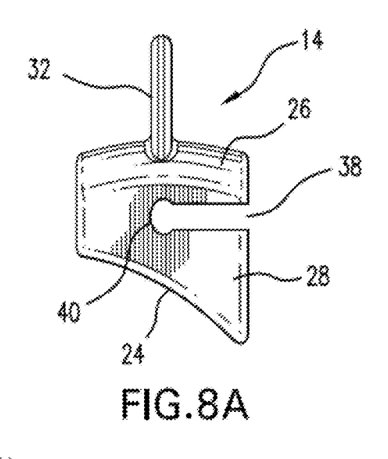
FIGS. 8A-C respectively show a front, side, and isometric view of the unit of the device that has a concave articulating surface, a bone contact surface having a keel structure, and at least one compression relief slot for absorbing compressive forces along the longitudinal axis of the spine.
Figure 8B:
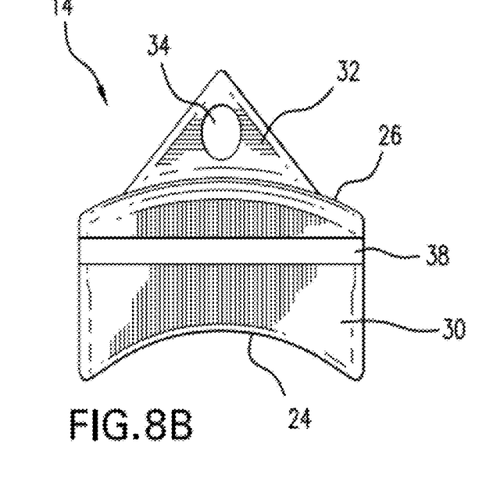
Figure 8C:
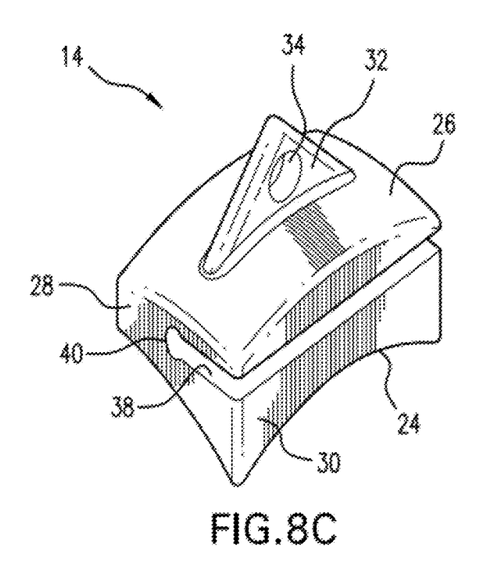

A first embodiment of the concave articulating surface unit (hereinafter, the "concave unit") 14 is shown in various aspect in FIGS. 3A-C. The concave unit 14 includes a concave articulating surface 24, which can be curved in a complementary manner to mate with and articulate with the convex articulating surface 16 of the convex unit 12. The concave unit 14 can also have a bone contacting surface 26, which can also be curved about two axes. As with the convex unit 12, the concave unit 14 can also have additional surfaces, which face anterior-posterior 28 and medial-lateral 30 and serve to contact and interface between the concave unit articulating surface 24 and the bone contacting surface 26.

The device can be provided with at least one bone contact augmentation structure 32, a preferred example of which can be a keel type structure, which for exemplary purposes only is shown in FIGS. 4A-C, 5A-C, 7A-C, 8A-C, 9A-C and 10A-D as projecting outwardly from the bone contacting surface at an approximate right angle. It is, however, within the inventor's concept that the contact augmentation structure can be any surface texture or any surface protrusion, such as the preferred exemplary keel structure that is placed into the bone material. The contact augmentation structure can also be an indentation into which bone material can grow or into which bone cement or some other material can be placed. Further, while the figures recited above show the exemplary keel structure as being essential at a right angle to the bone contacting surface of the convex unit or the concave unit to which it is attached, it is within the inventor's concept that the protruding structure or indentation can be multiple protrusions or indentations and can be at any variety of angles relative to the bone contacting structures.

Additionally, the keel structure or any alternative design for a protruding structure can be provided with at least one indentation or at least one through hole 34 defined in the structure. As shown in FIGS. 4B-C, 5B-C, 7B-C, 8B-C, 9B-C and 10C-D, the exemplary keel structure 32 defines a through hole, which can receive post-surgical bone growth and can at the time of implantation be provided with materials that promote through growth of bone material.

Alternative to or in augmentation of the protruding keel type structure, the bone contacting surface on either or both of the convex unit 12 and the concave unit 14 can be provided with at least one and preferably multiple spike 36 protrusions, which can promote fixation of the device into the adjacent bone material. While FIGS. 6A-C and 9A-C show the spike 36 protrusions as being essential at a right angle to the bone contacting surface of the convex unit or the concave unit to which it is attached, it is within the inventor's concept that the spike 36 protrusions can be at any variety of angles relative to the bone contacting surfaces 18, 26 from which they protrude.

As shown in FIGS. 7A-C, 8A-C and 9A-C the convex unit 12 or the concave unit 14 or both units can be provided with at least one compression relief slot 38 and additionally can be provided with living hinges 40, for the purpose of dampening compression forces and to provide translation along the longitudinal access or cranial-caudal axis of the spine. The cranial-caudal translation provided by the device equipped with at least one compression relief slot 38 and living hinge 40 mimics the normal tension and compression of the spine.

Figures 9A, 9B, 9C:
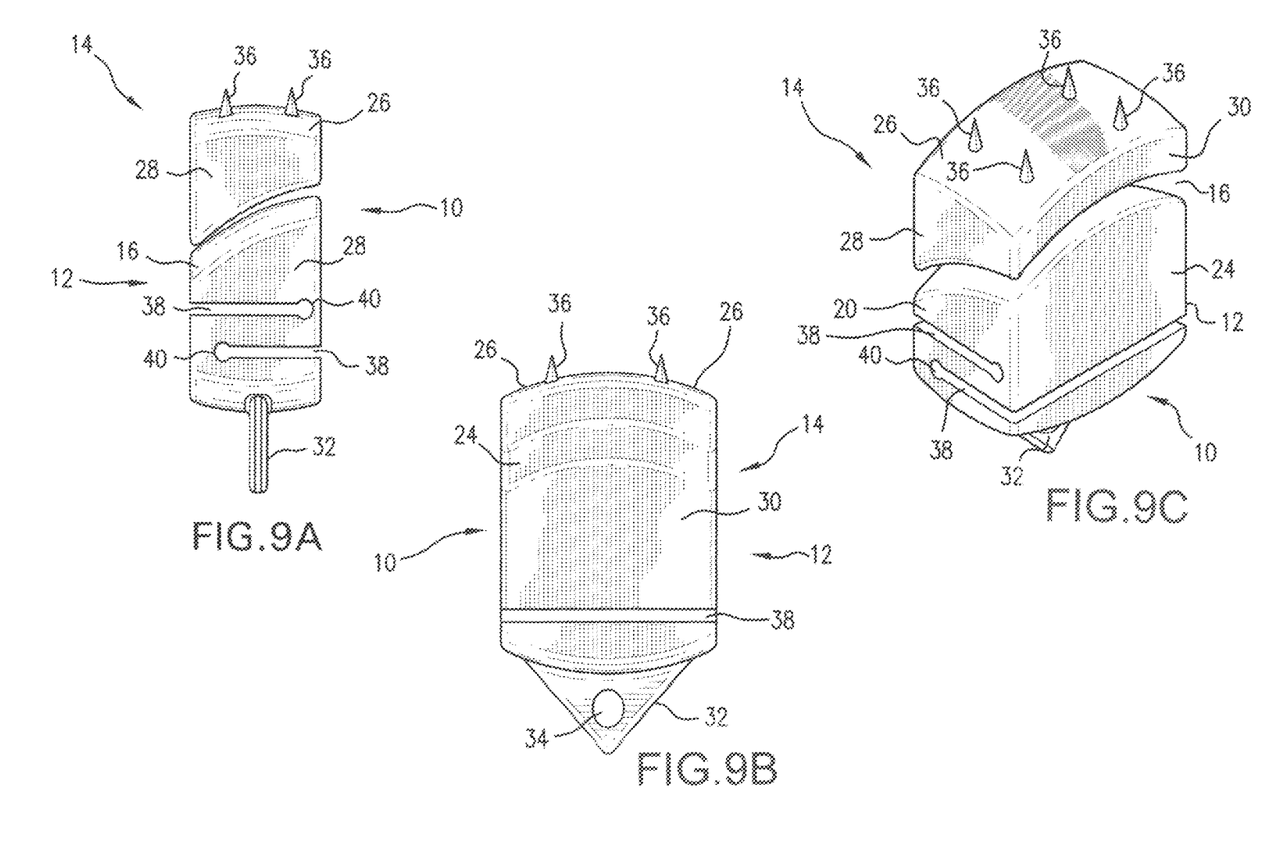
FIGS. 9A-C respectively show a front, side, and isometric view of a unilateral construct of the device, the device having at least two articulating surfaces on respective units of the device, the unit, which has a concave articulating surface having a bone contact surface with at least one spike and the unit, which has a convex articulating surface having at least one keel structure, the device having at least one compression relief slot.
Figure 10A:
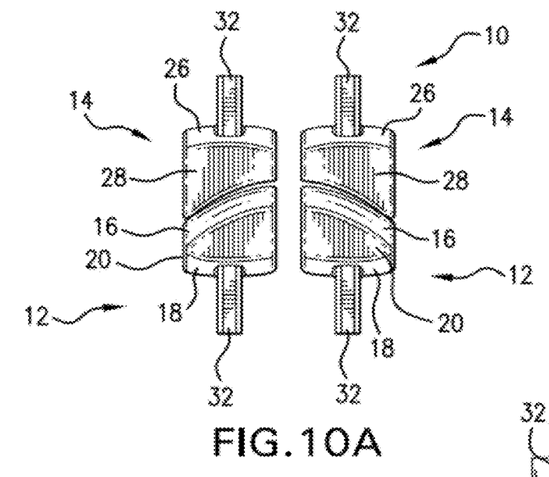
FIGS. 10A-D respectively show a front, top, side, and isometric view of a bilateral construct of the device, the construct having at least two devices, each of the devices having at least two articulating surfaces on respective units of each device, the unit, which has a concave articulating surface having a bone contact surface with at least one spike and the unit, which has a convex articulating surface having at least one keel structure.
Figure 10B:
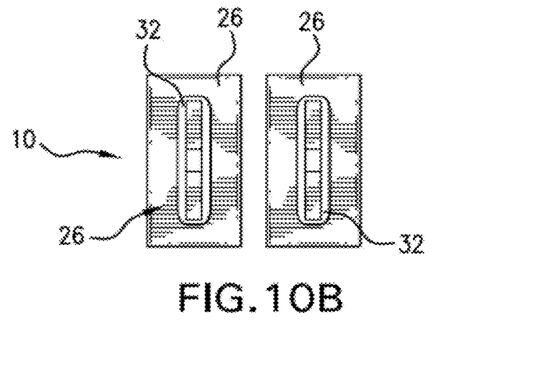
Figure 10C:
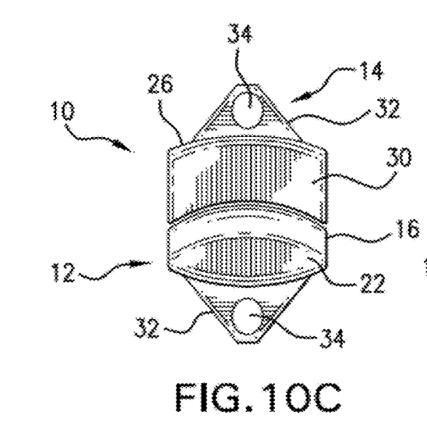
Figure 10D:
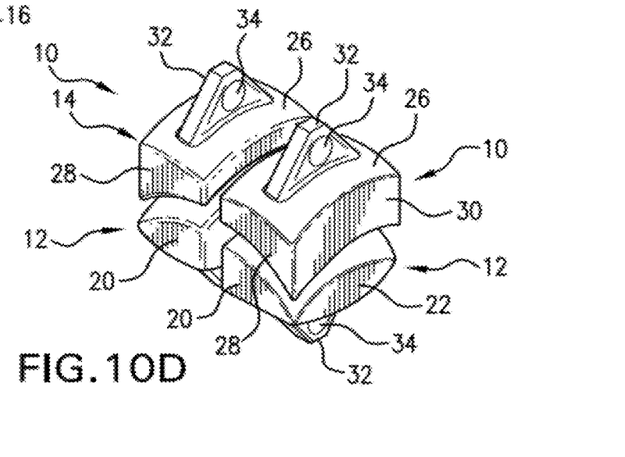

FIGS. 9A-C show the convex unit 12 inferiorly disposed in an articulating arrangement with the concave unit 14 of the device 10, such as would be found in an implanted device 10. It is within the inventor's conception that the inferior disposition of the implanted convex unit 12 relative to the concave unit 14 can be reversed if necessary as determined by the surgeon. A unilateral construct such as shown in FIG's 9A-C can include additional elements to include any or all of the features described above, such as the keel 32, the through hole 34, the spikes 36, the compression relief slot, 38, and the living hinge 40. Additionally the device 10 can be configured to be easily grasped by an insertion tool that can be provided to aid in the posterior approach implantation method of the invention.

FIG's 10A-D show two distinct devices 10, each having a respective pair of articulating units made up of a convex unit 12 and a concave unit 14, the combination of which provides a bilateral construct that can be implanted as needed in a patient. The exemplary bilateral construct shows both pairs of articulating units to be of identical configuration such that each of the devices 10 employed in the bilateral construct, when implanted are a mirror image one of the other across the sagittal plane of the body. If necessary, however, the two devices 10 that make up the bilateral construct can be differently configured, each separately including any or all of the additional features of the device, as discussed above. Preferably, the two devices will be of similar, if not identical, configurations. A bilateral construct, such as shown in FIG's 10A-D, represents a complete artificial disc replacement. In such a bilateral construct, the units, which contact the same vertebrae can be linked one to the other. The orientation of such a bilateral construct is important whereby surfaces 30 and 24 of the concave unit 14 and convex unit 12, respectively, are positioned lateral when the concave unit 14 is proximal or distal to the convex unit 12 of the device. As shown in FIG's 10A-D, this configuration provides a combined convex articulating surface for the bilateral construct that provides smooth articulation with the superiorly disposed combined concave articulating surface. It is within the inventor's conception that the inferior/superior relationship of the convex unit 12 and the concave unit 14 can be reversed.

The features of the device 10 can be embodied in various configurations and combinations, not all of which have been recited in the examples discussed herein. The components of the device 10 can be manufactured in various sizes of varying relative dimensions, cross-sectional geometry and varying radii of curvature for the articulating surfaces 16, 24 and bone contacting surfaces 18, 26. Furthermore, the radii of curvature of the opposing articulating surfaces need not be equal and a smaller radius of curvature for the convex unit 12 articulating surface 16 can facilitate translation anterior-posterior and medial-lateral. It is also within the understanding of the inventors that the geometry of the articulating surfaces of the opposing units of the device can be varied so as to define or restrict translation along the anterior-posterior and/or medial-lateral axes as desired. Exemplary of such variation of contact surface geometry as a means of limiting motion is the inclusion of walls in the geometry of a concave surface as is known in the art. Such variations in the device 10 can be used as necessary to improve the function of the device for the needs of a particular patient.

In addition to the surface features discussed herein, such as, for example keel structures 32 and spikes 36, any surface altering features, structures, or materials known in the art can be used to facilitate a strong device to bone connection for the implanted device. It is also within the inventors concept that other compression force absorbing devices known in the art can be employed in construction of the device 10 in addition or in place of the exemplary at least one compression relief slot 38 and living hinge 40 described herein.

The device 10 can be manufactured as integral components by methods known in the art, to include, for example, molding, casting, forming or extruding, and machining processes. It is also with the inventors' conception that the component units of the invention can be manufactured of different materials and using different methods such that the materials of the unit have different tensile strengths and compression absorbance qualities prior to assembly of the unit. The components can be manufactured having a variety of different dimensions so as to provide implantable replacement discs components that can be selected by the surgeon as being best suited to the anatomical size and conformation of individual patient's vertebrae. Manufacturing of the device components can be accomplished using suitable materials known in the art, such as, for example, implant grade metallic materials, such as titanium, titanium alloy, cobalt-chromium alloys, stainless steel, and the like. Additionally, the structures of the device 10 can be manufactured wholly or in part using non-metallic materials such as, for example, ceramic, PEEK, PEAK and artificial and natural bone materials. To promote low friction articulation of the opposing articulation surfaces 16, 24, increase the wear life of the device 10, and decrease particulate debris, the articulation surfaces 16, 24 can be provided with a highly polished finish. Further, other articulating interface materials can also be utilized such as Ultra High Molecular Weight Polyethylene (UHMWPE), an articulating surface material well known in the art.

The device 10 can be implanted as an artificial disc replacement and is designed to facilitate implantation using a posterior or transforaminal-posterior approach whereby the device 10 can be inserted through an open incision or through a minimally invasive incision. The instruments that can be employed to implant the device 10 can be configured to easily grasp and attach to the medial-lateral ends 22 or the anterior-posterior ends 20 so as to facilitate the immediate contact of the bone contacting surfaces 18, 26 to the vertebrate body upon insertion. Furthermore, the device 10 can be introduced in pairs as a bilateral construct, wherein the concave unit 14 and the convex unit 12 of the device are preassembled prior to implantation and the introducing instrument is configured to maintain the preassembled bilateral construct during the implantation thereof. It is also within the inventor's understanding of the invention, that the concept can also be applied to the implantation of articulating devices in other joints and areas of the human body that are in need of replacement surgery.

It is also within the concept of the present invention to provide a kit, which includes the at least one of the devices 10, which can be provided in various sizes, as well as tools to facilitate the surgical procedure and additional orthopedic components which can be employed to permanently or temporarily stabilize the vertebrae at the surgical site if necessary. Such a kit can be provided with sterile packaging to facilitate opening and immediate use in an operating room.

Each of the embodiments described above are provided for illustrative purposes only and it is within the concept of the present invention to include modifications and varying configurations without departing from the scope of the invention that is limited only by the claims included herewith.

What is claimed is:

1. A device for use in orthopedic surgery, comprising:
a pair of components positioned adjacent one another and defining a gap therebetween, each component including a first unit and a second unit, each of said units respectively having a bone contacting surface on one side of each of said units and an arcuate articulation surface on a second side of each of said units, said first and second sides being on opposing ends of each of said first and second units, said first and second units being sized and configured for implantation into a bone joint space of a subject, wherein said articulation surface of said first unit has a concave or convex shape and said articulation surface of said second unit is configured to have a convex or concave shape that is complementary to the shape of the first unit articulation surface; and
wherein, the articulation surfaces of the first units of the components cooperate to define a first radius of curvature and the articulation surfaces of the second units of the components cooperate to define a second radius of curvature, and wherein the second unit of each of the components includes a compression relief slot defined therein, the second units of each of the components defining mirror-image configurations relative to one another such that the compression relief slots cooperate with one another to translate compressive forces along the spine when implanted in a subject.

2. The device of claim 1, wherein at least one of said first and second units of at least one of said components is at least partially composed of a metallic material.

3. The device of claim 1, wherein at least one of said first and second units of at least one of said components is entirely composed of at least one metallic material.

4. The device of claim 1, wherein said first unit and said second unit of at least one of said components are composed of at least one metallic material.

5. The device of claim 1, wherein at least one of said first unit and said second unit of at least one of said components are at least partially composed of ceramic material.

6. The device of claim 1, wherein at least one of said first and said second unit of at least one of said components are composed of a non-bone material.

7. The device of claim 1, wherein the articulating surfaces of the first units of the components define a convex articulation surface and wherein the articulation surfaces of the second units of the components define a concave articulation surface.

8. The device of claim 7, wherein the first radius of curvature of said convex articulating surface defines a smaller radius than the second radius of curvature of said concave articulating surface, whereby said device is capable of translation along at least one axis said at least one axis being selected from the group consisting of anterior-posterior, medial lateral, and both anterior-posterior and medial-lateral.

9. The device of claim 1, wherein the first radius of curvature of the articulation surfaces of said first units is different from the second radius of curvature of said articulation surfaces of said second units.

10. The device of claim 1, wherein the articulation surfaces of each of said first and second units of at least one of said components allows translation in at least one direction.

11. The device of claim 1, wherein each of the second units of each component includes multiple compression relief slots said multiple compression relief slots being in an overlaying configuration relative one to the other.

12. The device of claim 11, wherein said at least one of said multiple compression relief slots includes a living hinge.

13. The device of claim 11, wherein the multiple compression relief slots include a first slot and a second slot, the first slot existing in a first plane, the second slot existing in a second plane, the first plane being parallel and spaced from the second plane.

14. The device of claim 1, wherein at least one of said bone contacting surfaces of said first and second units of at least one of said components comprises at least one protrusion.

15. The device of claim 14, wherein said protrusion is not at a right angle to said bone contacting surface.

16. The device of claim 14, wherein said protrusion is at least one spike type protrusion.

17. The device of claim 14, wherein said protrusion comprises at least one keel type protrusion and at least one spike type protrusion.

18. The device of claim 14, wherein both of said first unit and said second unit of at least one of said components further comprise said at least one protrusion respectively.

19. The device of claim 14, wherein said at least one protrusion is a keel type protrusion.

20. The device of claim 19, wherein the surface of said keel type protrusion comprises a textured or indented surface.

21. The device of claim 19, wherein said keel type protrusion defines a through hole.

22. The device of claim 21, wherein said through hole contains natural or artificial bone material.

23. The device of claim 21, wherein said through hole contains bone generation inducing material.

* * * * *